(12) United States Patent
Wermeling

(10) Patent No.: US 8,198,291 B2
(45) Date of Patent: Jun. 12, 2012

(54) INTRANASAL OPIOID COMPOSITIONS

(75) Inventor: Daniel Wermeling, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 12/755,691

(22) Filed: Apr. 7, 2010

(65) Prior Publication Data
US 2011/0118294 A1 May 19, 2011

Related U.S. Application Data

(63) Continuation of application No. 11/674,803, filed on Feb. 14, 2007, now abandoned, which is a continuation of application No. 10/647,789, filed on Aug. 25, 2003, now abandoned, which is a continuation-in-part of application No. 09/790,199, filed on Feb. 20, 2001, now Pat. No. 6,610,271, which is a continuation-in-part of application No. 09/569,125, filed on May 10, 2000, now abandoned.

(51) Int. Cl.
A01N 43/42 (2006.01)
A61K 31/44 (2006.01)

(52) U.S. Cl. ...................................... 514/282
(58) Field of Classification Search .................. 424/431
See application file for complete search history.

(56) References Cited

U.S. PATENT DOCUMENTS

| 3,812,853 A | 5/1974 | Crain |
| 4,464,378 A * | 8/1984 | Hussain ........................ 514/282 |
| 4,673,679 A | 6/1987 | Aungst et al. |
| 4,782,047 A | 11/1988 | Benjamin et al. |
| 4,889,860 A | 12/1989 | Rzeszotarski et al. |
| 4,946,069 A | 8/1990 | Fuchs |
| 4,950,664 A | 8/1990 | Goldberg |
| 4,973,596 A | 11/1990 | Cohen |
| 5,132,114 A | 7/1992 | Stanley et al. |
| 5,166,202 A | 11/1992 | Schweizer |
| 5,169,029 A | 12/1992 | Behar |
| 5,225,183 A | 7/1993 | Purewal et al. |
| 5,307,953 A | 5/1994 | Regan |
| 5,397,771 A | 3/1995 | Bechgaard et al. |
| 5,428,006 A | 6/1995 | Bechgaard et al. |
| 5,437,267 A | 8/1995 | Weinstein et al. |
| 5,529,787 A | 6/1996 | Merrill et al. |
| 5,543,434 A | 8/1996 | Weg |
| 5,577,497 A | 11/1996 | Mecikalski et al. |
| 5,622,166 A | 4/1997 | Eisele et al. |
| 5,629,011 A | 5/1997 | Illum |
| 5,637,314 A | 6/1997 | Sharpe et al. |
| 5,683,677 A | 11/1997 | Purewal et al. |
| 5,693,608 A | 12/1997 | Bechgaard et al. |
| 5,695,743 A | 12/1997 | Purewal et al. |
| 5,702,725 A | 12/1997 | Merrill et al. |
| 5,766,573 A | 6/1998 | Purewal et al. |
| 5,789,375 A | 8/1998 | Mukae et al. |
| 5,855,907 A | 1/1999 | Peyman |
| 5,866,143 A | 2/1999 | Elkhoury |
| 5,897,858 A | 4/1999 | Haslwanter et al. |
| 5,914,131 A * | 6/1999 | Merrill et al. ................... 424/473 |
| 5,948,389 A | 9/1999 | Stein |
| 5,958,379 A | 9/1999 | Regenold et al. |
| 5,998,434 A | 12/1999 | Mitch et al. |
| 6,013,633 A | 1/2000 | Balasubramanium et al. |
| 6,015,797 A | 1/2000 | Camborde et al. |
| 6,017,963 A | 1/2000 | Alfonso et al. |
| RE36,744 E | 6/2000 | Goldberg |
| 6,127,385 A | 10/2000 | Midha et al. |
| 6,193,985 B1 | 2/2001 | Sonne |
| 6,228,383 B1 | 5/2001 | Hansen et al. |
| 6,234,366 B1 | 5/2001 | Fuchs |
| 6,255,502 B1 | 7/2001 | Penkler et al. |
| 6,274,635 B1 | 8/2001 | Travis |
| 6,274,653 B1 | 8/2001 | Hecht et al. |
| 6,319,513 B1 | 11/2001 | Dobrozsi |
| 6,444,665 B1 | 9/2002 | Helton et al. |
| 6,608,073 B1 | 8/2003 | Hussain et al. |
| 6,610,271 B2 | 8/2003 | Wermeling |
| 6,713,470 B2 | 3/2004 | Jackson |
| 2001/0004644 A1 | 6/2001 | Levin |
| 2003/0077300 A1 | 4/2003 | Wermeling |
| 2003/0163099 A1 | 8/2003 | Wermeling et al. |
| 2003/0206867 A1 | 11/2003 | Wermeling |
| 2004/0115133 A1 | 6/2004 | Wermeling |
| 2006/0083691 A1 | 4/2006 | Wermeling |
| 2007/0209660 A1 | 9/2007 | Wermeling |

FOREIGN PATENT DOCUMENTS

| WO | WO90/02737 | 3/1990 |
| WO | WO02/11778 | 2/2002 |
| WO | WO2005/020906 | 3/2005 |
| WO | WO2007/231273 | 10/2007 |
| WO | WO2007231273 | 10/2007 |

OTHER PUBLICATIONS

Kippax, et al.; Applications for droplet sizing; Manual versus automated actuation of nasal sprays; Pharmaceutical Technology; 2004; p. 30, 32, 34, 36 and 38.

Illum, et al.; Intranasal delivery of morphine; The Journal of Pharmaceutical and Experimental Therapeutics; 2002; vol. 301:1; p. 391-400.

Pezron, et al.; Prodrug strategies in nasal drug delivery; Expert Opin. Ther. Patents; 2002; 12:3: p. 331-340.

Manjushree, et al.; Intranasal fentanyl provides adequate postoperative analgesia in pediatric patients; Can J Anesth; 2002; 49:2: p. 190-193.

(Continued)

Primary Examiner — Sreeni Padmanabhan
Assistant Examiner — Timothy E Betton
(74) Attorney, Agent, or Firm — Stites & Harbison PLLC; Richard S. Myers, Jr.

(57) ABSTRACT

The present invention relates to pharmaceutical compositions for intranasal administration to a mammal that contain an effective amount of an opioid, a liquid nasal carrier for the opioid, and optionally a sweetener, flavoring agent or masking agent. In some embodiments of the present invention, the pharmaceutical compositions have improved bioavailability. In other embodiments of the present invention, the opioid compositions improve patient compliance.

12 Claims, 5 Drawing Sheets

OTHER PUBLICATIONS

Ward-Smith, S.; Semi-automated testing of nasal sprays (Nasal Spray Testing); Pharmaceutical Technology Europe; 2002; p. 1-9.
A Brief History of Bristol-Myers Squibb; 2007; Newsroom.bms.com; p. 1-7.
Butorphanol Tartrate: Description; 2007; RXList, p. 1-2.
PCT Search Report; PCT/US01/14695, completed Jun. 25, 2001 (2 pages).
PCT Search Report; PCT/US04/27496, completed Dec. 20, 2004 (1 page).
PCT Preliminary Examination Report; PCT/US01/14695, completed Aug. 7, 2003 (7 pages).
PCT Preliminary Examination Report; PCT/US04/27496, completed May 15, 2006 (4 pages).
RXList, STADOL Butorphanol Tartrate drug warnings and precautions, [online] retrieved on Jan. 4, 2008, retrieved from http.//www.rxlist.com/cgi/generic/butor.htm, printed p. 1-5.
Loder, E. Cephalalgia, Post-marketing experience with an opioid nasal spray for migraine; lessons for the future; 2006; printed pp. 1-3, especially p. 2 (abstract only).

* cited by examiner

INTRANASAL OPIOID COMPOSITIONS

This application is a continuation of U.S. application Ser. No. 11/674,803, filed Feb. 14, 2007 now abandoned, which is a continuation of U.S. application Ser. No. 10/647,789, filed Aug. 25, 2003 now abandoned, which is a continuation-in-part of U.S. application Ser. No. 09/790,199 filed Feb. 20, 2001 now U.S. Pat. No. 6,610,271, which is a continuation-in-part of U.S. application Ser. No. 09/569,125 filed May 10, 2000, now abandoned. The entire disclosure of these applications is herein incorporated by reference.

BACKGROUND OF THE INVENTION

Pain is a major symptom of many diseases, (e.g., cancer, arthritis, neurological diseases, heart attacks, etc.). Inadequate treatment of pain can lead to depression, anger, fear of disease progression and in some extreme cases, suicide.

Unfortunately, a patient's non-compliance or failure to take medication as prescribed, has been linked to inadequate treatment of pain. This is not surprising, since many pain treatment regimens involve administering pain medications by injection route (e.g., intravenous (IV), intramuscular (IM) or subcutaneous injection). The intravenous route is normally regarded as one of the most in-convenient routes to administer pain medication to achieve rapid pain relief. Intravenous administration may cause non-compliance, because not only do patients fear getting the injection, but unpleasant experiences such as pain, irritation and infection resulting at the injection site may also lead to non-compliance.

The intranasal route is currently receiving special interest, especially in the area of pain management. When medication is administered via the intranasal route, the medication is applied to the nasal mucosa where it is absorbed. The extensive network of blood capillaries under the nasal mucosa is particularly suited to provide rapid and effective systemic absorption of drugs. The intranasal route of administration should achieve similar dose to plasma concentration (bioavailability) and efficacy to that of the intravenous route.

Intranasal administration of medication provides numerous advantages over the intravenous route. The principal advantages of intranasal route are non-invasive delivery, rapid drug absorption, and convenience. The intravenous route, unlike the intranasal route, requires sterilization of hypodermic syringes and, in the institutional setting, leads to concerns among medical personnel about the risk of contracting disease if they are accidentally stuck by a contaminated needle. Strict requirements for the safe disposal of needles and syringes have also been imposed.

In contrast, intranasal administration requires little time on the part of the patient and attending medical personnel, and is far less burdensome on the institution than injectable routes. There is no significant risk of infection of the patient or medical personnel in the institutional setting when dealing with the intranasal delivery of medication.

A second important advantage of intranasal administration over intravenous is patient acceptance of the intranasal delivery route. In some cases, the injections cause burning edema, swelling, turgidity, hardness and soreness. In contrast, intranasal administration is perceived as non-invasive, is not accompanied by pain, has no after-effects and produces prompt relief in the patient exhibiting pain symptoms. This is of particular advantage when the patient is a child. Many, if not most, patients experience anxiety and exhibit symptoms of stress when faced with hypodermic injections via the IM or IV routes. Further, most people have some familiarity with nasal sprays in the form of over-the-counter decongestants for alleviating the symptoms of colds and allergies that they or a family member have used routinely. Another important consideration is that the patient can self-administer the prescribed dosage(s) of nasal spray without the need for trained medical personnel.

Among the many medications available to treat pain, opioids (e.g., morphine, methadone, hydromorphone, butorphanol, etc.) play one of the most important roles. The major advantage of the opioids is that they have an extensive history of use and are much more effective in treating severe pain than other classes of medications e.g. aspirin, acetaminophen, ibuprofen, etc. Another major advantage is that opioids exhibit few adverse effects on organs such as the stomach, liver, or kidney, other than very minor problems such as nausea or constipation. This is a major benefit over other medications such as aspirin or anti-inflammatory drugs that may cause ulcers, kidney problems, high blood pressure, or liver inflammation. In addition to relieving pain, opioids have other beneficial effects, such as, for example, peripheral arterial vasodilation, when treating heart attacks, provides the benefit of reducing oxygen demand on the heart.

There are different intranasal opioid formulations known in the pharmaceutical arts. However, some intranasal opioid formulations have reduced bioavailability at conventional doses. These formulations require more pain medication to be administered to the patient or else the pain will be inadequately treated.

Given the problems associated with inadequate treatment of pain and patient noncompliance, there is a need for intranasal opioid compositions that have improved bioavailability. There is also a need for intranasal compositions that improve patient compliance.

SUMMARY OF THE INVENTION

In various embodiments, the present invention provides intranasal opioid compositions that have improved bioavailability when compared to intranasal prior art opioid compositions. In other embodiments, the present invention provides intranasal opioid compositions that improve patient compliance.

In one embodiment, the present invention provides a pharmaceutical composition for intranasal administration to a mammal; comprising: an effective amount of an opioid; a liquid nasal carrier for the opioid; and one or more sweeteners, flavoring agents, or masking agents or combinations thereof.

In another embodiment, the present invention provides a pharmaceutical composition having improved bioavailability for intranasal administration to a mammal; comprising: an effective amount of butorphanol; a preservative-free liquid nasal carrier.

In still another embodiment, the present invention provides a pharmaceutical composition having improved bioavailability for intranasal administration to a mammal; comprising: an effective amount of hydromorphone; a liquid nasal carrier having the essential absence of a preservative and the composition containing at least one sweetener, flavoring agent or masking agent.

In one preferred embodiment, the present invention provides a pharmaceutical composition for intranasal administration to a mammal; comprising: an effective amount of hydromorphone; a preservative-free liquid nasal carrier comprising sodium chloride, citric acid, water and at least one sweetener, flavoring agent or masking agent.

In still another preferred embodiment, the present invention provides a method of treating a mammal suffering from pain comprising intranasally administering to the mammal an effective amount of butorphanol or hydromorphone; a preservative-free liquid nasal carrier comprising sodium chloride, citric acid, water and at least one sweetener, flavoring agent or masking agent.

For a better understanding of the present invention together with other and further advantages and embodiments, reference is made to the following description taken in conjunction with the examples, the scope of which is set forth in the appended claims.

BRIEF DESCRIPTION OF THE FIGURES

Preferred embodiments of the invention have been chosen for purposes of illustration and description, but are not intended in any way to restrict the scope of the invention. The preferred embodiments of certain aspects of the invention are shown in the accompanying figures, wherein.

DETAILED DESCRIPTION OF THE INVENTION

Figure 1:
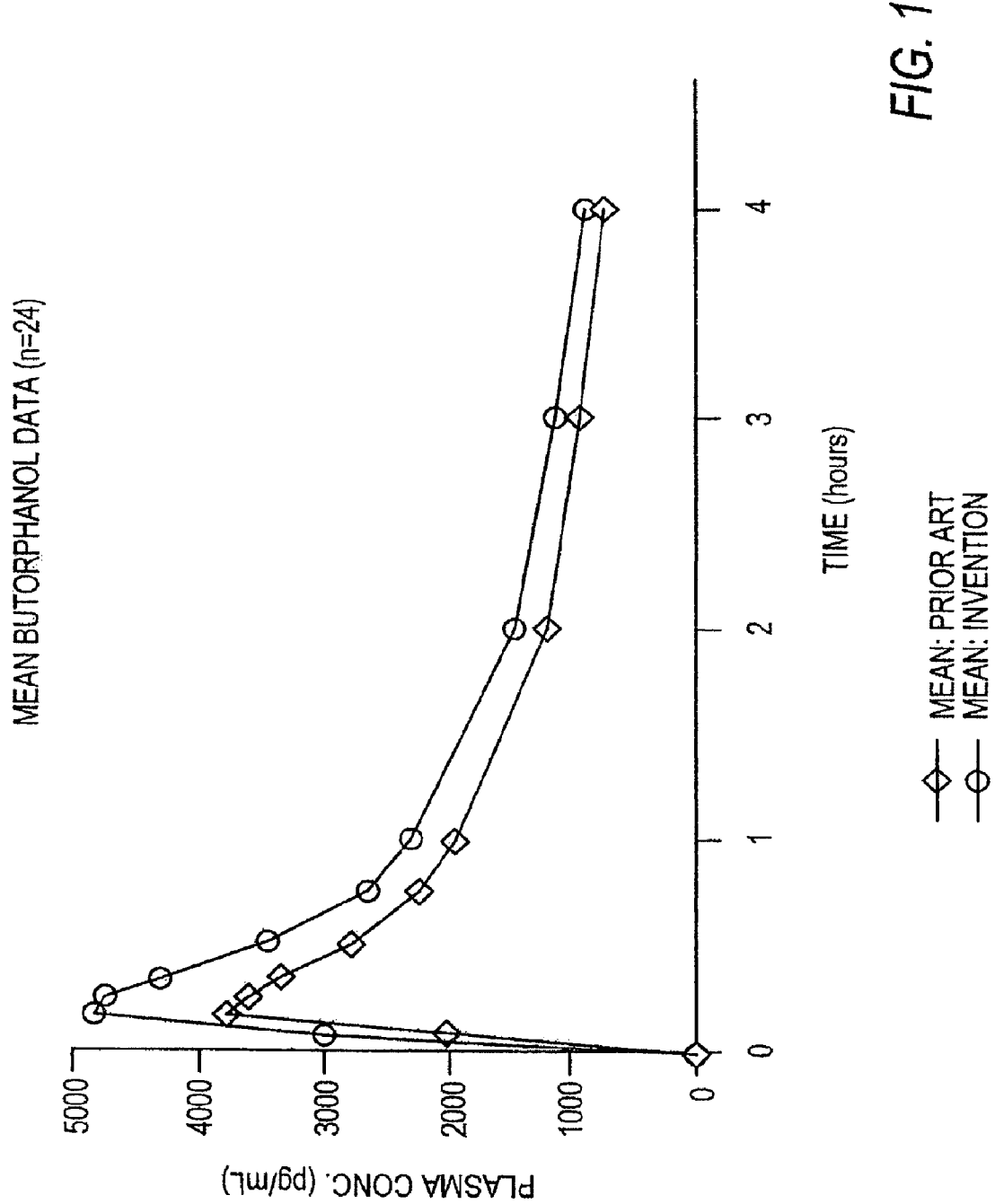
FIG. 1 is a graphic representation of the concentration of butorphanol in blood plasma versus time after administration of the test formulation from a unit-dose spray device (Invention)) and the administration of the test formulation in a multi-dose spray device (Prior Art).

The invention will now be described in connection with preferred embodiments. These embodiments are presented to aid in an understanding of the present invention and are not intended to, and should not be construed to, limit the invention in any way. All alternatives, modifications and equivalents that may become obvious to those of ordinary skill on reading the disclosure are included within the spirit and scope of the present invention.

In accordance with one embodiment of the present invention, it has now been surprisingly found that intranasal pharmaceutical compositions can be made having improved bioavailability in terms of plasma opioid levels. These intranasal compositions contain an opioid; and a liquid nasal carrier for the opioid. For example, it has been unexpectedly discovered, among other things, that at least about 10 to about 20% higher plasma levels of butorphanol can be achieved by administering an intranasal formulation from a unit-dose spray device. Improved bioavailability includes increases in plasma or serum opioid concentration when compared to prior art opioid formulations. Preferred increases include, but are not limited to, increases of more than 5% to 40% in bioavailability of the opioid.

Opioids as herein include any substance naturally or synthetically derived from opium. Suitable opioids for use in the present invention include, but are not limited to, morphine, apomorphine, hydromorphone, oxymorphone, dihydromorphine, levorphanol, levallorphan, levophenacylmorphan, norlevorphanol, nalorphine, nalbuphine, buprenorphine, butorphanol, naloxone, naltrexone, nalmexone, oxilorphan, cyclorphan, ketobemidone, fentanyl, sufentanil, alfentanyl, or combinations thereof. The most preferred opioids for use in the present invention include butorphanol and/or hydromorphone.

The opioid may be in free form or in pharmaceutically acceptable salt or complex form. Some examples of pharmaceutically acceptable salts of opioids include those salt-forming acids and bases that do not substantially increase the toxicity of the compound. Some examples of suitable salts include salts of alkali metals such as magnesium, potassium and ammonium. Salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

Intranasal opioid compositions of the present invention include a liquid nasal carrier. As used herein, "liquid nasal carrier" includes a solution, emulsion, or suspension designed for delivery of the opioid to the nasal mucosa. The liquid nasal carrier includes a diluent suitable for application to the nasal mucosa. Suitable diluents include aqueous or non-aqueous diluents or combination thereof. Examples of aqueous diluents include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil-in-water emulsions or water-in-oil emulsions. In the preferred butorphanol or hydromorphone compositions, the diluent is saline or water.

The nasal carrier of the present invention may also contain excipients such as antioxidants, chemical preservatives, buffering agents, surfactants and/or agents that increase viscosity. Antioxidants are substances that prevent oxidation of the formulations. Suitable antioxidants for use in the present invention include, but are not limited to, butylated hydroxytoluene, butylated hydroxyanisole, potassium metabisulfite, and the like.

In some embodiments of the present invention, the composition contains a preservative that is chosen in quantities that preserve the composition, but do not cause irritation of the nasal mucosa. Suitable preservatives for use in some embodiments of the present invention include, but are not limited to, benzalkonium chloride, methyl, ethyl, propyl or butylparaben, benzyl alcohol, phenylethyl alcohol, benzethonium, or combination thereof. Typically, the preservative is added to the compositions of the present invention in quantities of from about 0.01% to about 0.5% by weight.

In some embodiments of the present invention, the formulation is preservative-free. As used herein, preservative-free includes compositions that do not contain any preservative. Thus, the composition does not contain, for example, benzalkonium chloride, methyl, ethyl, propyl or butylparaben, benzyl alcohol, phenylethyl alcohol, or benzethonium.

If a buffering agent is employed in the composition, it is chosen in quantities that preferably do not irritate the nasal mucosa. Buffering agents include agents that reduce pH changes. Preferred buffering agents for use in the present invention include, but are not limited to, salts of citrate, acetate, or phosphate. The most preferred buffers include sodium citrate, sodium acetate, sodium phosphate, and/or combinations thereof. Typically, the buffer is added to the compositions of the present invention in quantities of from about 0.01% to about 3% by weight.

When one or more surfactants is employed, the amount present in the compositions of the invention will vary depending on the particular surfactant chosen, the particular mode of administration (e.g. drop or spray) and the effect desired. In general, however, the amount present will be of the order of from about 0.1 mg/ml to about 10 mg/ml, preferably about 0.5 mg/ml to 5 mg/ml and most preferably about 1 mg/ml.

The pharmaceutical compositions of the present invention may include one or more agents that increase viscosity chosen in quantities that preferably do not irritate the nasal mucosa and increase nasal retention time. Preferred agents that increase viscosity include, but are not limited to, methylcellulose, carboxymethylcellulose sodium, ethylcellulose, carrageenan, carbopol, and/or combinations thereof. The most preferred agents used to increase viscosity and increase nasal retention time is methylcellulose or carbopol. Typically, the agent that increases viscosity is added to the compositions of the present invention in quantities of from about 0.1% to about 10% by weight.

In some embodiments of the present invention, one or more sweetener or flavoring agents are employed. The sweetener or flavoring agent includes any agent that sweetens or provides flavor to the pharmaceutical composition: The sweetener or flavoring agent will mask any bitter or bad taste that may occur if the pharmaceutical composition drips back into the mouth after intranasal administration. By addition of a sweetener or flavoring agent to the intranasal composition, any barrier that a patient may have to taking the intranasal composition because of unpleasant taste is reduced. By adding a sweetener, flavoring agent or masking agent to the intranasal pharmaceutical composition of the present invention, patient compliance is enhanced or improved.

Preferred sweeteners or flavoring agents or masking agents to use in some embodiments of the present invention include, but are not limited to, acacia syrup, anethole, anise oil, aromatic elixir, benzaldehyde, benzaldehyde elixir, cyclodextrins, compound, caraway, caraway oil, cardamom oil, cardamom seed, cardamom spirit, compound, cardamom tincture, compound, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, glycyrrhiza, glycyrrhiza elixir, glycyrrhiza extract, glycyrrhiza extract pure, glycyrrhiza fluidextract, glycyrrhiza syrup, honey, iso-alcoholic elixir, lavender oil, lemon oil, lemon tincture, mannitol, methyl salicylate, nutmeg oil, orange bitter, elixir, orange bitter, oil, orange flower oil, orange flower water, orange oil, orange peel, bitter, orange peel sweet, tincture, orange spirit, compound, orange syrup, peppermint, peppermint oil, peppermint spirit, peppermint water, phenylethyl alcohol, raspberry juice, raspberry syrup, rosemary oil, rose oil, rose water, rose water, stronger, saccharin, saccharin calcium, saccharin sodium, sarsaparilla syrup, sarsaparilla compound, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Most preferred sweeteners to use in some embodiments of the present invention include, but are not limited to, saccharin, sodium saccharin, xylitol, mannitol, sorbitol, sucralose, maltodextrin, sucrose, aspartame, acesulfame potassium, dextrose, glycosides, maltose, sweet orange oil, dextrose, glucose, honey or combinations thereof. Most preferred flavoring agents to use in some embodiments of the present invention include, but are not limited to, glycerin, wintergreen oil, peppermint oil, peppermint water, peppermint spirit, menthol, syrup, or combinations thereof. Most preferred masking agents do not make contact with the taste buds. The preferred masking agent for use in the present invention includes, but is not limited to, cyclodextrins, cyclodextrins emulsions, cyclodextrins particles, cyclodextrins complexes, or combinations thereof.

The pharmaceutical compositions of different embodiments of the present invention may of course also include additional ingredients, such as pharmaceutically acceptable surfactants, co-solvents, adhesives, agents to adjust the pH and osmolarity.

The pharmaceutical compositions of the present invention are not limited to any particular pH. However, generally for nasal administration a mildly acid pH will be preferred. The pH ranges from about 3 to 6 are preferred, more preferred pH ranges are from about 3 to about 5, and most preferred pH ranges are from about 4 to about 5. If the adjustment of the pH is needed, it can be achieved by the addition of an appropriate acid, such as hydrochloric acid, or base, such as for example, sodium hydroxide. In the preferred embodiments of the present invention, butorphanol or hydromorphone formulations, have a pH of about 5.0 and a pH of about 4, respectively.

The pharmaceutical composition in some embodiments of the present invention can be made, for example, by mixing the opioid with a liquid nasal carrier and/or a sweetener, flavoring agent, or masking agent or combinations thereof at room temperature under aseptic conditions to form a mixture. In other embodiments of the present invention, the mixture is filtered. It will be understood by those of ordinary skill in the art that the order of mixing is not critical, and the present invention includes without limitation mixing of the formulation in any order.

Pharmaceutical compositions of the present invention can be administered intranasally by nasal spray, drop, solution, suspension, gel, and the like. In one preferred embodiment, the pharmaceutical composition of the present invention is a sterile solution or suspension.

When the pharmaceutical composition is a liquid, preferred volumes of the liquid are absorbed through the nasal mucosa. The preferred volume of the liquid includes volumes of from about 0.025 ml to about 2 ml, more preferably, from about 0.25 ml to 1 ml, and most preferably from about 0.05 ml to about 15 ml in an adult and smaller for children. However, the pharmaceutical compositions of the present invention are not limited to one particular volume.

Preferred devices for intranasal delivery of pharmaceutical compositions of the present invention are available from, for example, Pfeiffer of America of Princeton, N.J. and Valois of America, Inc. of Greenwich, Conn. These devices are preferred because they have the capability of consistently delivering the pharmaceutical composition. These devices are easily operable by the patient, leave virtually no opioid remaining in the device after use and can thereafter be discarded without concern that others may abuse the opioid or other controlled substance.

The device can be filled with single or multidose amounts of opioids. Preferably, the device is filled with one single dose of opioid. In a preferred embodiment, the container holding the pharmaceutical composition and its sealing means are sterilizable, most preferably, at least parts of the device that are in contact with the pharmaceutical composition is constructed and assembled in a configuration that can be sterilized. Devices with one or more unit-dose(s) can be sterilized either before or after packaging, employing methods and technology that are well known in the art. Individual devices can be packaged, sterilized and shipped; alternatively, entire shipping and storage packages can be sterilized at once, and the devices removed individually for dispensing, without affecting the sterility of the remaining units.

The amount of opioid that can be intranasally administered in accordance with the composition and methods of the present invention will depend on the particular opioid chosen, the condition to be treated, the desired frequency of administration and the effect desired. As used herein, an effective amount of opioid includes that amount effective to achieve the relief or palliation of symptoms, condition and/or diseases associated with pain. Some diseases and/or conditions that cause pain include, but are not limited to, cancer, arthritis, neurological diseases, heart attacks, trauma, childbirth, migraines, or surgery.

Maximal dosage of the pharmaceutical composition of the present invention for a mammal is the highest dosage that elicits analgesia or anesthesia, which does not cause undesirable or intolerable side effects such as respiratory depression. The minimal dose of the opioid is the lowest dose that achieves the desired result. In any event, the practitioner is guided by skill and knowledge in the field, and the present invention includes without limitation dosages that are effective to achieve the pain relieving effect in the mammal. Preferred doses of opioids for intranasal administration include, but are not limited to, hydromorphone HCL from about 0.1 mg to about 30 mg; butorphanol tartrate from about 0.1 to about 10.0 mg; fentanyl citrate from about 5 mcg to about 500 mcg; methadone HCl from about 0.5 to about 50 mg; oxymorphone HCL from about 0.1 mg to about 30 mg; and morphine HCL from about 1 mg to about 40 mg.

The intranasal opioids of the present invention can be used, for example, to elicit analgesia or an analgesic response to relieve or alleviate pain. The opioids of the present invention may also be used to produce anesthesia or an anesthetic response where the mammal experiences loss of feeling or sensation, especially loss in pain sensation, to permit the performance of surgery or other painful procedures. The opioid is administered to a mammal suffering from a condition and/or disease that require opioid treatment. Mammals include, for example, humans, as well as pet animals such as dogs and cats, laboratory animals, such as rats and mice, and farm animals, such as horses and cows.

EXAMPLES

The examples below demonstrate improved bioavailability of illustrative compositions of the present invention when delivered from a unit-dose spray device compared to the same compositions when delivered from a multi-dose spray device. The examples also show pharmaceutical compositions that include sweeteners, flavoring agents, or masking agents or combinations thereof, which can improve patient compliance.

Example 1

This example compares bioavailability of a butorphanol formulation when administered using a unit-dose or multi-dose delivery device. The formulation contains 10 mg butorphanol tartrate, 6.5 mg sodium chloride, 1.0 mg citric acid, 0.20 mg benzethonium chloride in purified water with 1.2 mg sodium hydroxide and hydrochloric acid added to adjust the pH to 5.0. The multi-dose sprayer purports by its label to administer 0.1 ml of liquid composition by metering upon activation by the user. The formulation had the following function and properties when administered to human subjects via the Pfeiffer Unitdose Second Generation spray device. Administration of a 2 mg dose of butorphanol tartrate produced a $T_{max}$ (hr) of about 0.234 (range about 0.083 to about 0.333); a $C_{max}$ (pg/ml) of about 5230 (range of about 2393 to about 8478); an $AUC_{(0-t)}$ of about 10661 pg*hr/ml (range of about 5351 to about 17722). Administration using the multi-dose spray pump produced a $T_{max}$ of 0.245 hr, a $C_{max}$ of 4072 pg/ml and an $AUC_{(0-t)}$ of 9329 pg*hr/ml.

The second delivery system employed to administer the butorphanol compositions was a unit-dose disposable intranasal applicator that is commercially available from Pfeiffer of America under the designation "Unitdose Second Generation." Each of the Pfeiffer spray applicators was charged with sufficient liquid to deliver a 0.1 mL dose of the butorphanol test formulation. The glass containers were filled using a pipette under clean conditions, sealed and assembled to the applicator. Each of the applicators was weighed prior to use and after use. Qualified medical personnel administered, one dose into each nostril, after which the applicator was recovered for weighing. In the case of the unit-dose applicators (test formulation), two devices were used for each patient, both of which were discarded following the post-use weighing. The results of these studies of the method and system of the invention and the comparative prior art method follow.

TABLE I

Sample Characteristics of Dose Weight Delivery.

| Delivery System | N | mean wt. gms | std. dev. | std. error | minimum | maximum |
|---|---|---|---|---|---|---|
| Unit-Dose | 23 | 0.206 | 0.00660 | 0.00138 | 0.193 | 0.223 |
| Multi-Dose | 24 | 0.180 | 0.0285 | 0.00582 | 0.114 | 0.220 |

Unit-Dose:

The statistical comparison of dose 1 and dose 2 for the test formulation unit dose delivery system was done using a paired t-test. Analysis of the data indicated that the difference between the mean, sprays of the two applications using the Pfeiffer device was not statistically significant (t=1.0; p=0.3). The sample of 23 sprayers (actually 23 sets of 2 sprayers, since they were single-dose) had a mean total dose for two sprays of 0.206 grams with a standard deviation of 0.00660 grams.

Multiple-Dose:

The total dose dispensed by two sprays was recorded. The sample of 24 multi-dose sprayers had a mean total dose for two sprays of 0.180 grams with a standard deviation of 0.0285 grams.

Comparison of Average Total Dose:

The two-sample t-test for the comparison of the unit-dose and multi-dose sprayers indicated a statistically significant difference between the mean total doses taking into account the size of the sample. The unit-dose mean total dose was significantly closer to the prescribed target and dose than the multi-dose mean total dose (t=4.3; p<0.001). A 95% confidence interval for the difference in means is (0.0140, 0.0380).

Comparison of Variability:

The F test for the comparison of variances revealed that the variability in the total doses dispensed by the multi-dose sprayer was significantly higher than the variability in weights dispensed by the unit-dose sprayer (F=18.7; p<0.001). The variability in the multi-dose sprayer is 18.6 times that of the unit-dose sprayer. High variability in dose delivery leads to higher rates of adverse drug effects at excessive dose and inadequate treatment if the dose is low. Both consequences harm the patient hence the goal is to precisely deliver the prescribed dose.

Comparison of Each Sprayer to the Standard of 0.2 Grams

A t-test was used in each case to compare the observed sample mean to the desired weight of 0.2 grams. The unit-dose sprayer dispensed a mean total weight that was significantly higher than the goal of 0.2 grams (t=4.4; p<0.001). A 95% confidence interval for the mean total weight dispensed by the unit-dose sprayer is (0.203, 0.209). The multi-dose sprayer dispensed a mean total weight that was significantly lower than the goal of 0.2 grams (t=3.4; p<0.003). A 95% confidence interval for the mean total weight dispensed by the multi-dose sprayer is (0.168, 0.192). Based on the above, the unit-dose delivery system of the test formulation exhibits a much higher degree of accuracy in intranasally administering the volume of liquid composition corresponding to 0.1 gm: +3% vs −10%.

Bioequivalence

This example assesses the bioequivalence of a butorphanol formulation administered from the unit-dose or multi-dose sprayers described above. The test formulation comprises 1 ml of STADOL NS containing 10 mg butorphanol tartrate, 6.5 mg sodium chloride, 1.0 mg citric acid, 0.20 mg benzethonium chloride in purified water with 1.2 mg sodium hydroxide and hydrochloric acid added to adjust the pH to 5.0. The multi-dose sprayer accompanying STADOL NS purports, by its label, to administer 0.1 ml of liquid. The unit-dose delivery device delivers 0.1 ml of liquid.

The second analysis was to determine whether the intra-subject variabilities of the two spray devices are equal. The study was initiated with 16 subjects, 15 of which completed the study to provide data for this analysis; one subject dropped out after the second period. The following analysis considers both raw and normalized data, with the latter standardized with respect to the dose dispensed.

For both the raw and normalized data, log transformations are applied to the pharmacokinetic endpoints Cmax, AUC (00891 ast), and AUC(inf.). A mixed effects model was considered for each parameter. Fixed effects for the factors sequence (4 levels), period 3 levels) and formulation (2 levels) were included in the model. Additionally, gender, as well as the interactions between gender and each of sequence, period and formulation was included as a factor in each model to determine whether separate analyses would be necessary for males and females. A total of seven models were considered: Tmax, log of raw Cmax values, log of normalized Cmax values, log transformed values for raw and normalized AUC (last), and log values for raw and normalized AUC(inf.). In all cases, the interaction between gender and formulation was not significant, indicating that separate models for males and females were not warranted. In addition, the lack of significance of the effects included in each model indicate that there was no evidence of unequal carryover between the delivery system of the prior art and that in one embodiment of the present invention.

Figure 2:
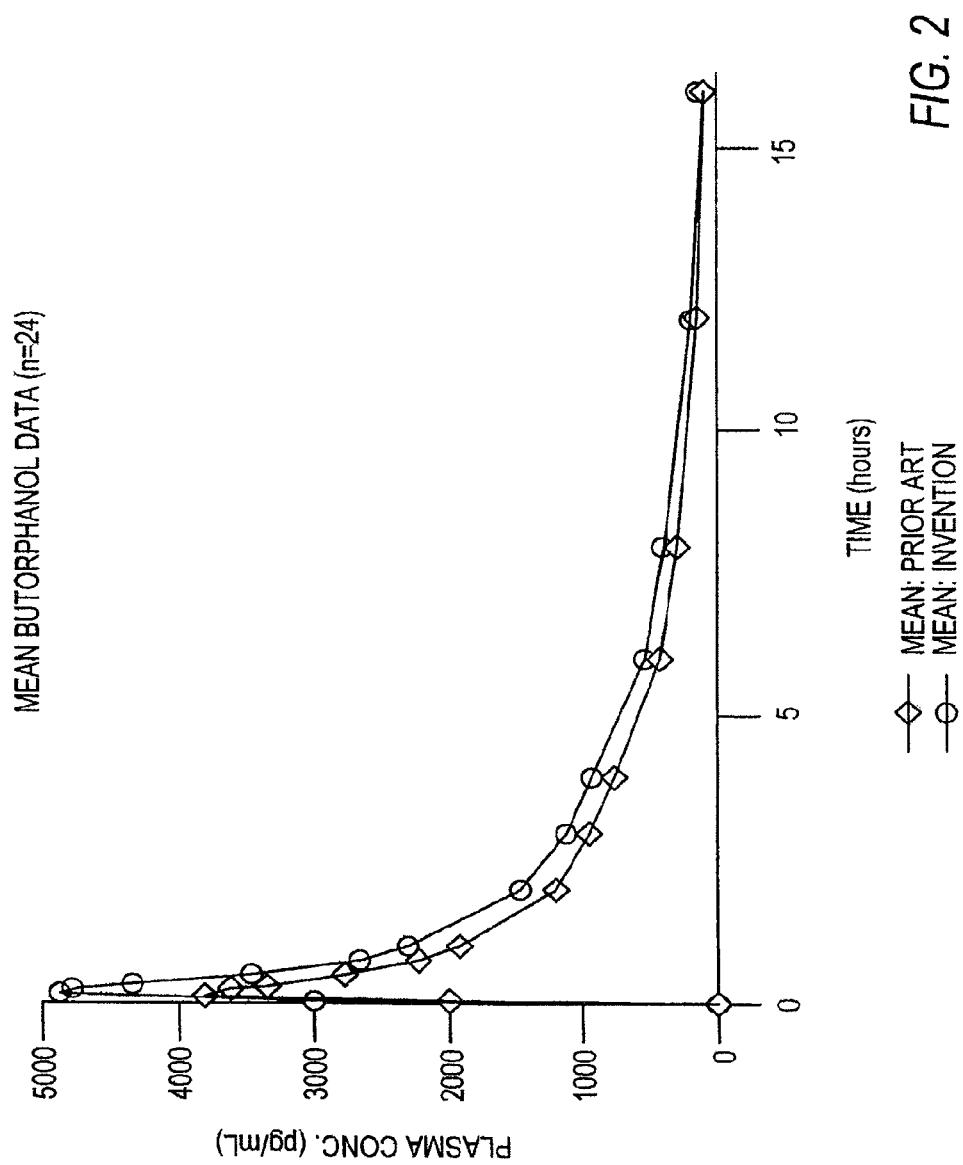
FIG. 2 is a graphic representation of the data of FIG. 1 over a longer time period.

The mean levels of butorphanol from analysis of the subject's blood plasma reported in pg/ml are plotted against time in FIGS. 1 and 2. The concentration of drug for the unit-dose was unexpectedly higher than that of the multi-dose system. The testing for bioequivalence was done using the method of two one-sided t-test (as described by Bolton, S., *Pharmaceutical Statistics*. Marcel Dekker, Inc., New York, 1997, pages 415 ff.). For each parameter, the 90% confidence interval for the ratio of the test unit-dose to reference multi-dose devices appear in Table 2 below.

TABLE 2

Summary of the two one-sided hypothesis tests for PK parameters

| Parameter | Lower Conf Limit for Ratio of Test/Reference | Upper Conf Limit for Ratio of Test/Reference |
|---|---|---|
| Tmax | 0.749 | 1.132 |
| log (Cmax)* | 1.031 | 1.855 |
| log (AUClast)* | 1.037 | 1.540 |
| log(AUCinf)* | 1.050 | 1.461 |
| log(normCmax)* | 0.897 | 1.589 |
| log(AUClast)* | 0.921 | 1.290 |
| log(normAUCinf)* | 0.937 | 1.220 |

*Note:
The actual confidence limits obtained for these parameters have been exponentiated since the data were log-transformed originally.

Since none of these confidence intervals for the non-standardized data are contained in the interval from 0.8 to 1.25, the conclusion is that the two (test and reference) are not equivalent when compared on raw values. For $T_{max}$, the one-sided t-test for $H_O$: Test/Reference <0.8 is not rejected. Also, the tests of $H_O$: Test/Reference >1.25 are not rejected for any of the log-transformed raw values. While the normalization by dispensed doses does improve the comparability of the two devices, two of the three parameters fail to reject the null hypothesis $H_O$: Test/Reference >1.25. Bioequivalence is supported only by the pair of one-sided tests for the normalized, log-transformed AUC(inf). Both one-sided t-test for each of the seven parameters have been performed at an alpha level of 0.05.

The data show that the FDA-approved (STADOL NS) product that has been sold and dispensed for a number of years unexpectedly delivers below label strength. The degree of variability is also significantly greater than that of the method of the invention using the Pfeiffer device. Since the test formulation administered from the unit-dose device achieves higher drug serum concentration, the small excess in unit-dose administration can be further reduced by adjusting the volume and/or drug concentration placed in the delivery device. Thus, the drug container can actually be filled with less drug.

Equality of Variances

The Pitman-Morgan adjusted F test was used to compare variances of the unit-dose and multi-dose parameters. (See Chow, S-C. and Liu, J-P, *Design and Analysis of Bioavailability and Bioequivalence Studies*. Marcel Dekker, Inc., New York (2000)). Since this test could not be generalized to the three period design, the first two periods of the butorphanol trial were used, and for the purposes of this analysis, there are two delivery systems, two periods, and two sequences. The Pitman-Morgan adjusted F test can be used even if the period effect is significant, and has a simplified form in the absence of period effects. Of the seven PK parameters considered, only $T_{max}$ exhibited a significant period effect. Table 3 summarizes the results of the tests of equality. The null hypothesis is that the variances are equal, and small p-values are indicative of a departure from equality.

TABLE 3

Summary of the Pitman-Morgan's adjusted F tests for PK parameters

| Parameter | Pitman-Morgan F Value | p-value |
|---|---|---|
| Tmax | 0.3 | 0.6 |
| log (Cmax) | 11.3 | 0.005 |
| log (AUClast) | 30.1 | <0.0001 |
| log (AUCinf) | 15.3 | 0.002 |
| log (normCmax) | 8.4 | 0.01 |

TABLE 3-continued

Summary of the Pitman-Morgan's adjusted F tests for PK parameters

| Parameter | Pitman-Morgan F Value | p-value |
|---|---|---|
| log (AUClast) | 23.7 | 0.0002 |
| log (normAUCinf) | 10.7 | 0.0005 |

The tests of equality variances indicate that for all PK parameters except Tmax, the variabilities of the two dose systems are significantly different, with the unit dose system demonstrating much lower variability of drug levels in the blood. While the normalization of the $C_{max}$, AUC(last) and AUC(inf) parameters somewhat decreased the difference between the variances (as evidenced by slightly smaller F values), the variances were nonetheless significantly different. The variability associated with the unit-dose system was smaller than that of the multi-dose system of the prior art, which is consistent with the findings of the delivery volume weight study.

From the above, it is apparent that the dose weight/volume data is confirmed by the blood level (pharmacokinetic) analysis. The formulation administered from the multi-dose device results in an area under the curve that is 90% of the test formulation of the present invention. Thus, the test device achieves 10% higher area under the curve and 10% higher serum levels as compared to the reference device. This difference is highly significant from a patient therapy standpoint. When FDA-prescribed bioequivalence statistical methods are applied, it is concluded that—the products as administered to the patients are not equivalent. Thus, the unit-dose device in one embodiment of the present invention provides an unexpected improvement in the intranasal administration of butorphanol.

As will be understood by one of ordinary skill in the art, the results and conclusions drawn above from the study of the intranasal administration of butorphanol can be extended in the practice of the invention to other opioids that can be administered intranasally in the form of a liquid spray. Moreover, the compositions and methods of the present invention can be practiced to the advantage and benefit of patients, of medical facilities and medical professionals, and of society at large for the intranasal administration of other opioids and controlled substances.

The formulation substantially as described immediately above was prepared but did not contain benzethonium chloride. This formulation had the following spray pattern function when sprayed from the Pfeiffer Unitdose Second Generation device onto an impaction plate from at various distances. At a spray distance of 1 cm the spray had an average maximum diameter ($D_{max}$) of about 2.3 cm (range 2.2-2.4), an average minimum diameter ($D_{min}$) of about 2.1 cm (range 2.0-2.2) and an average ovality of about 1.1 (range of 1.0 to 1.2; 9.1% RSD). At a spray distance of 3 cm the spray had an average maximum diameter ($D_{max}$) of about 5.2 cm (range of 4.2-6.1), an average minimum diameter ($D_{min}$) of about 4.6 cm (range of 3.8-5.8) and an average ovality of about 1.1 (range of 1.0-1.3; 9.2% RSD). At a spray distance of 5 cm, the spray had an average maximum diameter ($D_{max}$) of about 7.9 cm (range of 7.0-8.4), an average minimum diameter ($D_{min}$) of about 7.2 cm (range of 5.8-8.0) and an average ovality of about 1.1 (range of 1.0 to 1.2; 6.6% RSD).

At a spray distance of 1 cm from a detection laser beam, the spray has a droplet size distribution having a mean Dv10 of about 15.45 μm (range of 13.70 to 19.98), a mean Dv50 of about 41.46 μm (range of 35.74 to 55.67) and a mean Dv90 of about 93.88 μm (range of 69.55 to 117.15). The spray had a mean span [(Dv90-Dv10/Dv50)] of about 1.76 (range of 1.55-1.91).

At a spray distance of 3 cm, the spray had a droplet size distribution having a mean Dv10 of about 13.83 μm (range of 11.84 to 15.68), a mean Dv50 of about 35.29 μm (range of 29.46 to 41.69) and a mean Dv90 of about 90.80 μm (range of 71.2 to 122.42). The spray had a mean span [(Dv90-Dv10/Dv50)] of about 2.17 (range of 1.92-2.56).

At a spray distance of 5 cm, the spray had a droplet size distribution having a mean Dv10 of about 15.82 μm (range of 14.38 to 17.17), a mean Dv50 of about 32.96 μm (range of 31.03 to 35.32) and a mean Dv90 of about 71.85 μm (range of 61.64 to 83.68). The spray had a mean span [(Dv90-Dv10/Dv50)] of about 1.69 (range of 1.50-1.90).

The formulation had the following function and properties when administered to human subjects via the Pfeiffer Unit-dose Second Generation spray device. Administration of a single 2 mg dose of butorphanol tartrate produced a $T_{max}$ (hr) of about 0.25 (range of 0.167 to about 0.5); a $C_{max}$ (ng/ml) of about 2.08 to about 4.68; and an $AUC_{(0-t)}$ of about 7.6 to about 11.41 ng*hr/ml.

Example 2

Hydromorphone Intranasal Solution

In accordance with the composition and methods described above, hydromorphone HCL (HM HCL) was formulated in a liquid composition for use in the practice of one embodiment of the invention. HM HCL is a potent mu-receptor agonist opiate analgesic with properties similar to morphine. HM HCL is chemically similar to morphine, oxymorphone, and codeine and shares many of their analgesic and pharmacological properties.

HM HCL is a prescription drug narcotic analgesic, more commonly known by the trade name of DILAUDID® (Merck Index, 1983). Dilaudid ($C_{17}H_{19}O_3N.H_2O$) was discovered by the A.G. Knoll chemical firm of Ludwigshafen, Germany and was the subject of a 1923 patent. The first literature describing the synthesis and testing of this medication appeared in the 1920's and it has been used in the clinical management of pain since then. The first extensive literature review was published in 1933 by the Council on Pharmacy and Chemistry in the *Journal of the American Medical Association* (Eddy, N. B. Dilaudid (Dihydromorphoninone hydrochloride) J Am Med Assoc 1933; 100: 1032-1035). The drug is approved and widely accepted in the medical community as a safe and effective analgesic. It is presently marketed under the trade name Dilaudid® and Dilaudid-HP by Abbott laboratories.

It is known that HM HCL is subject to hepatic first pass metabolism when administered orally or by suppository. Thus, when administered intranasally, the effective unit-dose can be substantially less as compared to doses administered by oral or rectal routes.

The HM HCL is preferably prepared in the form of a single or unit-dose nasal spray for intranasal administration by a precision dosage manually activated pump. Each 1 ml of nasal spray solution is preferably formulated to contain 10 mg HM hydrochloride with 0.2% sodium chloride, 0.2% sodium citrate, 0.2% citric acid solution, and sterile water (i.e., water for injection, USP), accepted antioxidant concentration and buffer in pharmaceutical products. The pH of this formulation was approximately pH 4.0. This formulation was used in the hydromorphone clinical study below.

As will be understood by those familiar with the art, dosage forms at lower concentrations of hydromorphone can be prepared for administration based upon the patient's lower body weight, as in the case of children or adults of substantially smaller size. The nasal spray solution has a pH in the range of from about 3 to about 7, with a pH of about 4-5 being preferred.

In a preferred delivery system, each actuation of the nasal spray pump delivers 0.1 ml of this 10 mg/ml HM HCL solution constituting a 1 mg dose. A smaller dose may be administered to children. The filled applicators can be sterilized by methods well known in the art. The HM HCL nasal spray applicators are stored at 15°-30° C. (59°-86° F.) and protected from light to provide for maximum shelf life. Since the applicator body is not transparent, visual inspection of the drug product for signs of deterioration is not possible and attention to the expiration date and storage conditions is important. Any expired product is discarded in the appropriate manner.

An analysis of previous work describing intranasal (IN) administration of narcotics suggested that HM HCL is highly likely to have good bioavailability by the IN route in view of its potency and water solubility. Extensive review of hydromorphone literature did not reveal any comparative IV/IM/IN concentration versus time or pharmacokinetic data. A protocol was designed to determine the bio-availability of HM HCL by the IM and IN routes by comparing the pharmacokinetics of intramuscularly administered HM HCL and intranasally administered HM HCL to HM HCL administered via the IV route. Specifically, the objectives of this study were: (1) to compare the pharmacokinetics of HM via intranasal, intramuscular, and intravenous administration of a 2 mg dose of HM HCL; and (2) to evaluate the bioavailability of 2 mg HM HCL after intranasal, IM and IV routes of administration using a standard three-period, crossover design.

A formulation of HM HCL for intranasal administration was prepared in the form of a liquid composition at a concentration of 1.0 mg of HM HCL in 0.1 L. The composition was used to fill the required number of single-dose, metered sprayers commercially produced and sold by Pfeiffer of America, Inc. Each subject received a single spray in each nostril for a total of 2.0 mg. A 2.0 mg dose is preferred as being within common, safe and labeled doses prescribed for pain management. Commercially available HM HCL (Dilaudid® for parental administration from Knoll Pharmaceutical Company) was purchased for IM/IV administration.

Investigational Methods

Nine healthy male subjects between the ages of 22 and 33 years participated in this inpatient study. Study participants were selected based on inclusion/exclusion criteria, history and physical exam, laboratory tests, and other customary procedures. Subject demographics were recorded. These included age range: 22-33 years; height range: 168-188 cm; weight range: 70.3-95.3 kg; origin: six Caucasian, two Asian, one Native American; all were non-smokers. All nine of the subjects completed the study according to the protocol. Each of the subjects received 3 doses of 2 mg of HM HCL on three separate occasions. No clinically significant protocol violations occurred during this study. Because the inclusion criteria mentioned abstinence from prescription and non-prescription drugs prior to and during the study, any medications taken in the 14 days before the study and during the study were noted.

Clinical Trials

Study Drug Formulation: HM HCL for intranasal administration was supplied by the University of Kentucky College of Pharmacy. HM HCl for intravenous administration was supplied as Dilaudid® 1 mg/mL for subjects 1, 3, 8, and 9 on the first day and for subjects 2, 4, 5, 6, 7 on the second study day. HM HCl for intramuscular administration was supplied as Dilaudid® 4 mg/mL for subjects 2, 4, 5, 6 and 7 on first study day and for subjects 1, 3, 8 and 9 on the second study day. Free base content was 1.77 mg or 88.7% of stated HM HCl strength (from molecular weights: 321.8−36.46=285.34, 285.34/321.8=88.7%). To summarize, the dosages for each of the three routes of administration were as follows.

Treatment A: 2.0 mg intravenous HM HCL
Treatment B: 2.0 mg intramuscular HM HCl; and
Treatment C: 2.0 mg intranasal HM HCl solution Study Drug Administration On days 1 and 8, 2.0 mg of HM HCl was given intravenously or intramuscularly in random order following an overnight fast. On day 15, 2.0 mg of HM HCl was given intranasally following an overnight fast (except for water ad lib). Subjects were not permitted to recline for 4 hours following drug administration and remained fasting for 4 hours (until lunch) on these study days.

Meals and snacks prepared by the University of Kentucky Hospital Dietetics and Nutrition department were provided for each subject. Subjects were instructed to eat all of their meals. All subjects received identical meals and snacks on each of the treatment days, but received different meals on the different study days.

Safety Measures

Weight, blood pressure, and pulse were measured prior to dosing and at the end of the study. Blood pressure and pulse rate were measured with the subjects seated in an upright position before any corresponding blood sample was collected. Blood pressure and pulse rate were measured and recorded on the same arm throughout the study at 0 (pre-dose) and 30 minutes, 1, 2, 4, 8 and 16 hours.

Clinical Adverse Events

Spontaneously reported adverse events were recorded by the subjects throughout the study; adverse events were also elicited by non-directed interviews.

Sample Collection

Blood samples for period I through period III were collected from each subject according to the following schedule: 0 (pre-dose), 5, 10, 15, 20, 30 and 45 minutes, and 1, 2, 3, 4, 6, 8, 12 and 16 hours following HM HCl administration. The beginning of the IV administration was considered time zero. After collection, the blood was centrifuged in a refrigerated centrifuge at 4° C. to separate the plasma and the cells and the plasma was transferred to polypropylene tubes. The plasma was stored at approximately −70° C. at the study site until shipped to an independent analytical service. The plasma was maintained frozen during shipping and upon arrival at the remote analytical facility, the samples were stored at approximately −20° C. until analyzed.

Bioanalytical Methods

LC/MS/MS Assay for Hydromorphone

The sample analysis was performed by an independent service in accordance with established protocols. Concentrations less than 20 pg/mL were reported as below quantitation limit (BQL). Samples with concentrations greater than 2,000 pg/mL were reanalyzed using a dilution so that the assayed concentration was within the range of 20 to 2,000 pg/mL. QC samples were also diluted. During the validation, the precision was expressed as the percent coefficient of variation (% CV) and the accuracy as the percent difference from the theoretical (same as relative error).

Pharmacokinetic Methods

Plasma concentration versus time data for HM were analyzed using non-compartmental pharmacokinetic methods.

Maximum plasma concentration ($C_{max}$) and the corresponding sampling time ($T_{max}$) were identified by observation. Concentration versus time data were plotted on a semilogarithmic scale and the terminal log-linear phase was identified by visual inspection. The elimination rate constant (ë$_z$) was determined as the slope of the linear regression for the terminal log-linear portion of the concentration versus time curve. The terminal half-life value (t$_{1/2}$) was calculated as 0.693 divided by ë$_z$.

The area under the curve plotting plasma concentration versus curve (AUC) was calculated by the trapezoidal rule and extrapolated to infinite time. The AUC to the last time point (AUC$_{0-last}$) was computed by the linear trapezoidal rule. Mean plasma concentration were calculated for graphical presentation only. Data included in the mean calculation were for samples with measurable concentrations drawn within 5% of the nominal sampling time.

Safety Results

Results of the clinical measurement of vital signs and body weight exams were recorded and nasal exams were performed. A review of this data failed to reveal any clinically significant safety concerns. There were no serious adverse events and no subjects were discontinued due to adverse effects. Subjects commented that the intensity of the drug effects were lower with the IN route compared to the IV or IM administrations.

Bioanalytical Results

Hydromorphone in Plasma by LC/MS/MS Results from the control samples and calibration curves analyzed with the study samples and the method validation was reported: The overall CV, which reflects precision was <7.4% for the QC samples. The percent recovery ranged from 94.5 to 100, 1% for QC concentrations 200.0, 500.0, and 1000 which reflects accuracy was <6% for the QC samples.

Pharmacokinetic Results

Figure 3:
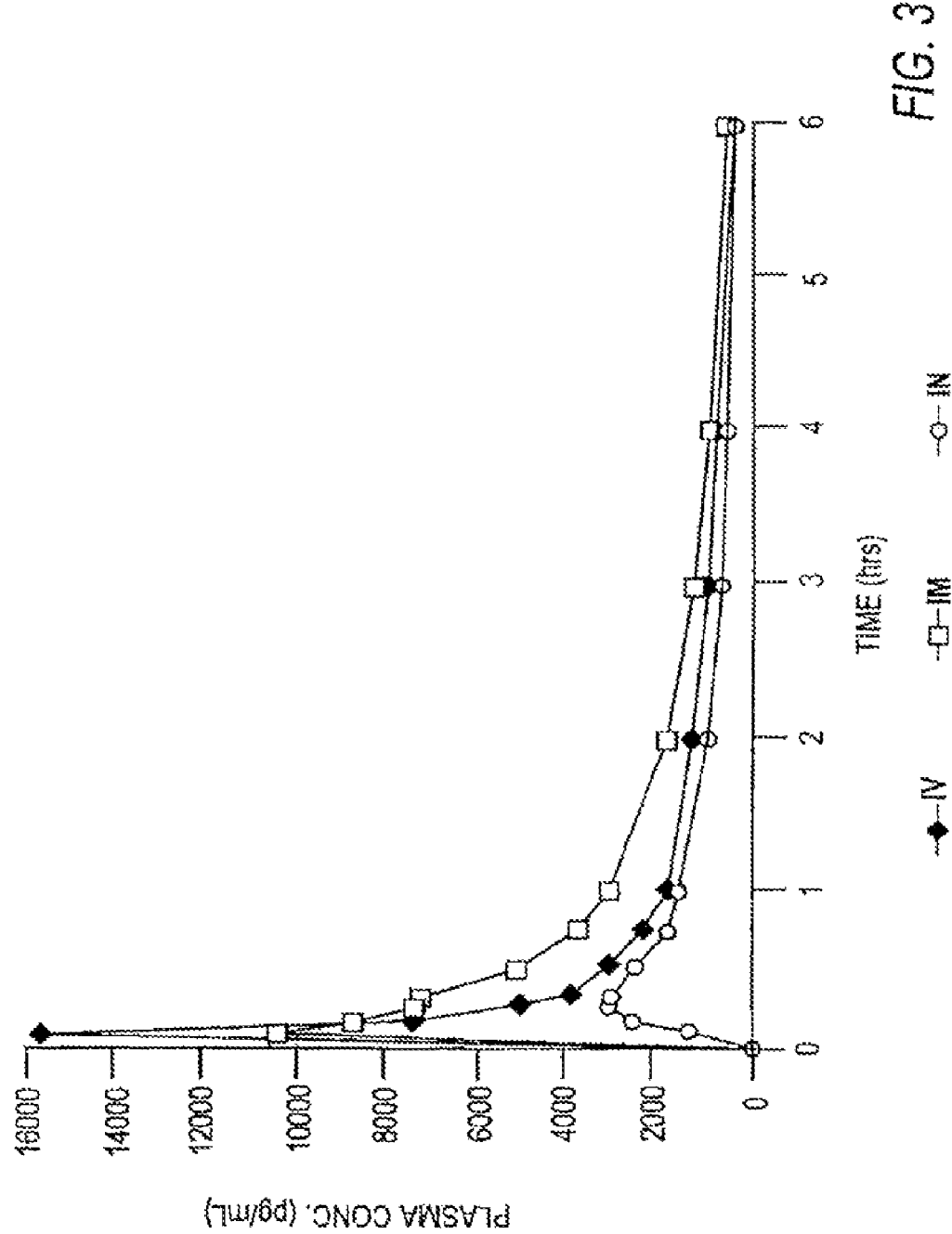
FIG. 3 is a graphic representation of the concentration of hydromorphone in blood plasma versus time for IV, IM and intranasal (IN) doses (mean (n=9) Hydromorphone concentration versus time graphs following IV, IM, and IN doses of 2 mg Hydromorphone HCI (6 hrs after dose).
Figure 4:
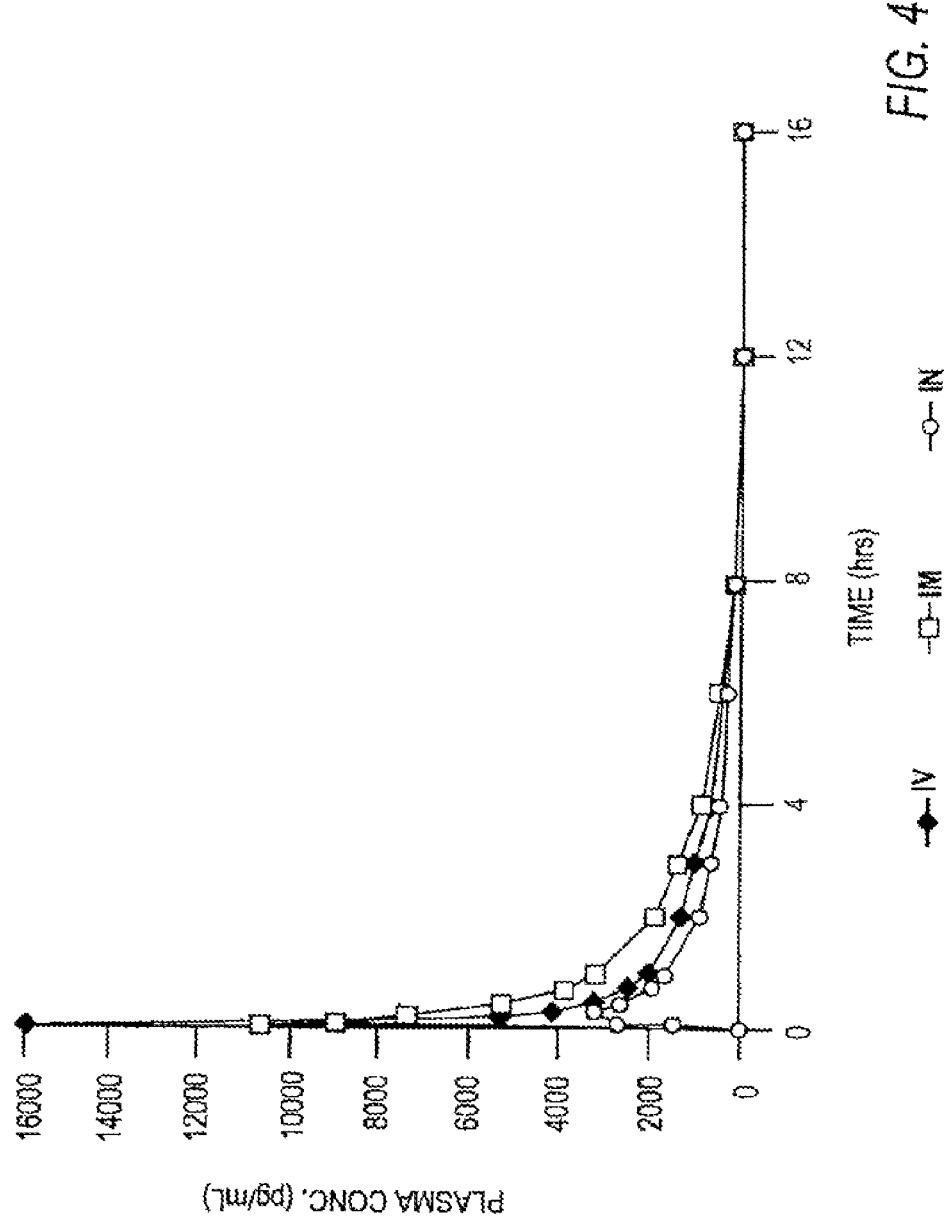
FIG. 4 is a graphic representation of the data of FIG. 3 over a longer period of time (mean (n=9) Hydromorphone concentration versus time graphs following IV, IM, and IN doses of 2 mg Hydromorphone HCI (16 hrs after dose).
Figure 5:
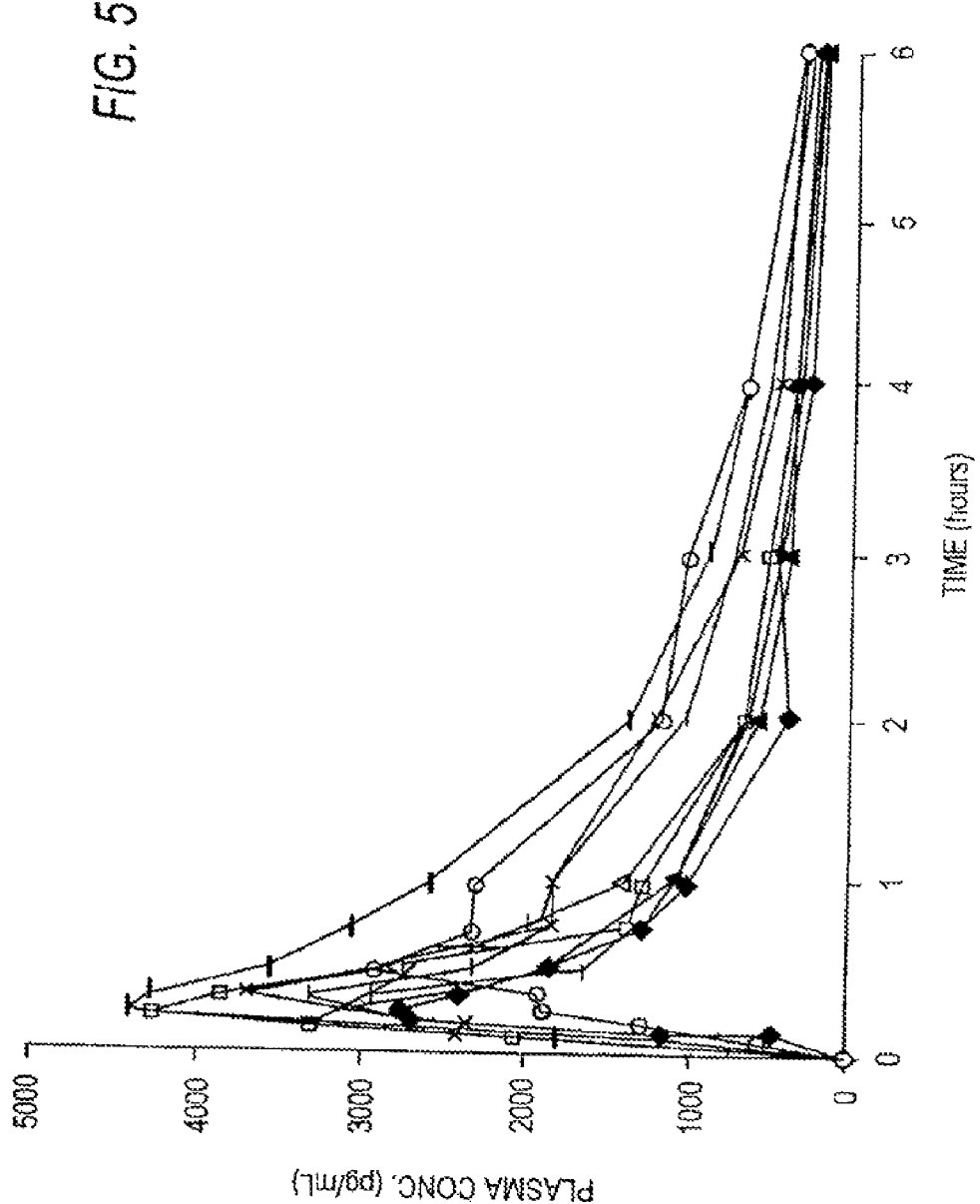
FIG. 5 is a graphic representation of the concentration of hydromorphone in blood plasma versus time for a group of subjects (graph of Hydromorphone concentrations versus time following IN doses of 2 mg Hydromorphone HCI to 9 subjects.

The plasma hydromorphone HCL concentrations and actual collection times for each of the 9 subjects was tabulated and plasma concentration-time curves for each of the 9 subjects were prepared. Mean concentration-time curves of FIGS. 3 and 4 are representative for most subjects (mean data tabulation). FIG. 3 is a plot of the mean (n=9) hydromorphone concentration versus time graphs following IV, IM and IN doses of 2 mg hydromorphone HCL during the 6 hours after dose; FIG. 4 is the same data plotted for 16 hours after the dose. Curves for all subjects for 6 hours after the IN dose appear in FIG. 5 as a graph of hydromorphone concentrations versus time following IN doses of 2 mg hydromorphone HCl to 9 subjects.

Non-compartmental pharmacokinetic analysis was used to evaluate the plasma concentration versus time curves of hydromorphone following single 2.0 mg doses of hydromorphone HCL by intravenous (IV), intramuscular (IM), and intranasal (IN) routes. Individual plasma hydromorphone concentrations versus time profiles for all subjects were recorded; the number of time points used to estimate the elimination rate constant were also recorded; and a complete listing of individual and mean pharmacokinetic parameters for all 9 subjects was recorded.

Rapid absorption of hydromorphone HCl was observed after the IM and IN doses. The T$_{max}$ values were approximately 9 and 18 minutes, on average, for the IM and IN doses, respectively. The mean T$_{max}$ for the IV infusion was not the first blood sample after the end of the infusion for two reasons. The peak concentration after the IV dose in one subject was not at the first blood sample after the end of the IV infusion, but at the next time point. In the case of Subject 4, acquiring the blood sample immediately following the IV infusion was delayed resulting in the mean T$_{max}$ being affected. As expected, the hydromorphone C$_{max}$ and AUCs were significantly higher after IM and IV administration compared to IN administration. Mean plasma half-lives and clearance (after correcting for bioavailability) were similar for all three treatments.

The arithmetic mean value of absolute bioavailability of hydromorphone from the IN formulation is 64%. The range was 50% to 81% bioavailability compared to the IV dose. The apparent bioavailability of the IM hydromorphone HCL was about 30% greater than that of the same dose of IV administration. The source of this aberrant phenomenon was not found, but unusual distribution phenomena after parenteral administration have been reported by others working in this field.

Statistical Evaluation

The pharmacokinetic parameters in Table 4 were analyzed to evaluate the effect of routes of administration and to test for period and sequence effects. The analysis of this pilot data is considered in two parts: the first part considers only the first two periods and includes the factors of treatment, sequence (i.e., a test of carryover effects) and period; the second part contains all three periods and treatments, but ignores the effects of sequence and period. The 2-period analysis is noted in Table 4 as period 1 vs. 2 and the last column contains the 3-period model.

There are even more significant treatment effects for these nine outcomes. Post-hoc analyses are based on Fisher's least significant difference procedure and displayed in Table 4. In light of the fact that there were no significant period or sequence effects (using an alpha level of 0.05), and since this is a pilot project, it is arguable that the above analysis is appropriate.

Since the C$_{max}$ value for Subject 07 was beyond 2 standard deviations of the mean with all measurements included, there is an objective method for omitting this value for this subject. Analyses with and without this outlier gave the same result.

TABLE 4

Summary of significance levels from IN 2-period and 3-period model

| Parameter | Sequence (1 vs 2) | Period (1 vs 2) | Treatment IV vs IM | Treatment (IV vs IM vs IN) |
|---|---|---|---|---|
| T$_{max}$ | NS* | NS | NS | .0001 |
| C$_{max}$ | NS | 0.32 | 0.71 | .0001 |
| C$_{max}$ (omit outlier) | NS | 0.62 | NS | .0001 |
| AUC$_{0-t}$ | NS | NS | .0001 | .0001 |
| AUC$_{0-\infty}$ | NS | NS | .0001 | .0001 |
| t$_{1/2}$ | NS | NS | NS | NS |
| CL/F | NS | NS | .0001 | .0001 |
| Dose | NS | NS | .0001 | .0001 |
| ë$_z$ | NS | NS | NS | NS |

*All p-values reported as NS are >0.1.

In this study of nine healthy male subjects that received 2 mg hydromorphone HCL by IV, IM and IN routes, comparisons between the IM and IN doses for purposes of bioequivalence could not be completed when it was found that the hydromorphone concentrations for the IM dose were markedly different as compared to those from the IN doses.

Noncompartmental analysis of the pharmacokinetic data gave results similar to previous studies with respect to half-lives, clearance, rapid distribution into the tissues, and large apparent distribution volume (Parab et al. 1988; Hill et al. 1991), although comparisons between this study and previous studies should be done with caution because of differences in analytical techniques. Hydromorphone HCL is well absorbed by the nasal route. Intranasal bioavailability was approximately 64%, on average. Interindividual variation was smaller for C$_{max}$ and T$_{max}$ for the IN route compared to the IV and IM routes. Three compartment characteristics were suggested by the tri-phasic concentration versus time curves, but compartmental analysis was not performed.

After the short IV infusion, the hydromorphone concentrations peaked at the end of the infusion as expected in all but one subject. Peak concentrations after the IM dose were unexpectedly rapid and precluded the analysis of the data for showing the bioequivalence of the IM and IN doses, and that analysis was not pursued.

Pharmacokinetic parameter estimates yielded CVs less than 27% for IN parameters except for $V_{SS}$ (CV 46%). Estimates of within-subject variability were smaller than estimates for published studies of IV hydromorphone HCL (Parab et al.; Hill et al.; Vallner et al.). Using a crossover design and standardizing meal times in this study likely helped to lower within-subject variability.

Clearance is similar for all three routes of administration regardless of route. Variabilities in CL and $V_{SS}$ estimates are less after the IV dose compared to the IN dose. The reduced variability is expected since IV dosing avoids between-subject variability in absorption and first-pass metabolism.

Adverse events were less frequent and milder after the IN dose compared to the IV and IM doses. Assuming a dose-response relationship, this effect believed to be attributable to the fact that the bioavailability of the IN dose was less and the peak concentration lower, so the subjects effectively received a lower dose that was more slowly absorbed. Nasal irritation was not observed with the exception of a bad taste in the throat reported by most subjects after the IN dose. In summary, hydromorphone HCL is well absorbed by the nasal route with bioavailability of 64%. $C_{max}$ and $T_{max}$ were similar for IM and IV routes. Clearance is similar regardless of route.

Hydromorphone HCL produced no systemic adverse events beyond those commonly experienced by injection. After single IN doses the subjects complained of bitter taste as the only local administration effect of the formulation. The bitter taste can be masked by the addition of a sweetener to the formulation. Detailed nasal examination demonstrated no pathology of the naso-pharynx after single administration of the HM HCL formulations.

In a further series of studies, hydromorphone HCL is going to be administered in accordance with the method of the invention as described above to larger groups of volunteers selected from the following categories.
1. in good health, ages 18 to 40;
2. in good health ages 60 to 80;
3. patients with rhinitis;
4. post-partum breast feeding for milk transfer;
5. post-operative pain in women;
6. children and adolescents with cancer;
7. male knee surgery patients; and
8. male and female surgical patients.

The results of these studies indicate the, HM HCL is suitable for use in providing relief from pain in a wide variety of settings without adverse side effects that are any more significant than those reported for the alternate routes of administration, and provides the advantages of convenience, and rapid onset.

Liquid formulations are prepared as fully dissolved solutions in a nasal carrier of each of the following systemic analgesics: morphine, apomorphine, metopon, oxymorphone, desomorphine, dihydromorphine, levorphanol, cyclazocine, phenazoeine, levallorphan, 3-hydroxy-N-methyltiaorphinan, levophenacylmorphan, meazocine, norlevorphanol, phenomorphan, nalorphine, nalbuphine, buprenorphine, pentazocine, naloxone, naltrexone, diprenorphine, nalmexone, cyprenorphine, alazoeine, oxilorphan, cyclorphan, ketobemidone, apocodeine, profadol, cyclorphan, cyprenorphine, dihydromorphine, pholcodine, hydroxypethidine, fentanyl, sufentanil and alfentanyl.

Clinical testing of each of the above liquid compositions in accordance with the method of the invention as practiced in the hydromorphone HCL clinical test using a Pfeiffer unit-dose applicator produces results comparable to those obtained in the hydromorphone HCL work.

Example 3

This example described preferred intranasal compositions of the present invention. The opioid can be dissolved in nasal carrier that includes a diluent, buffer system, antioxidant, one or more agents to control viscosity, and sweetener, flavoring agent or masking agent. The dosage and volume to be intranasally administered can be adjusted according to patient specific parameters (for example, weight, age, kidney and liver function, etc.). Preferred agents and ranges of the intranasal compositions are listed below and can be selected from each group.

1. Opioid (One or More)

| | |
|---|---|
| Hydromorphone HCl | 0.1-30 mg |
| Butorphanol tartrate | 0.1-10.0 mg |
| Fentanyl Citrate | 5-200 mcg |
| Methadone HCl | 0.5-50 mg |
| Oxymorphone HCl | 0.1-30 mg |
| Morphine HCl | 1-40 mg |

2. Buffer (One or More-Optional)

| | |
|---|---|
| Sodium citrate | 0.01-5% |
| Sodium acetate | 0.01-5% |
| Sodium phosphate | 0.01-5% |

3. Anti-Oxidant (Optional):

| | |
|---|---|
| Butylated hydroxytoluene | 0.01-5% |

4. Sweetener, flavoring or masking agent (one or more),

| | |
|---|---|
| A sugar, such as sucrose | 0.1-5% |
| Aspartame | 0.1-5% |
| Saccharin | 0.1-5% |
| An oil, such as wintergreen, orange | 0.1-5% |
| Menthol and/or camphor | 0.1-5% |

5. Viscosity Control (One or More-Optional)

| | |
|---|---|
| Methylcellulose | 0.1-10% |
| Carbopol | 0.1-10% |

6. Diluent
QS with Water or Saline to the Desired Volume

Having now generally described the invention, the same may be more readily understood through the following reference to the following example, which is provided by way of illustration and is not intended to limit the present invention unless specified.

What is claimed is:

1. An intranasally deliverable pharmaceutical composition comprising: an effective amount of hydromorphone or a pharmaceutically acceptable salt thereof and a liquid nasal carrier that is preservative-free, wherein the pH of the composition is from about 3 to about 6, and wherein upon intranasal administration of the composition containing at least 2 mg to about 10 mg of the hydromorphone or the salt thereof, the subject exhibits a $C_{max}$ hydromorphone plasma concentration of at least about 3000 pg/mL.

2. An intranasally deliverable pharmaceutical composition comprising an effective amount of hydromorphone or a pharmaceutically acceptable salt thereof, and a preservative-free liquid nasal carrier comprising sodium chloride, citric acid, and water, wherein the pH of the composition is from about 3 to about 6.

3. A method of treating a mammal suffering from pain comprising intranasally administering to the mammal the composition of claim 1 or 2.

4. The pharmaceutical composition of claim 1 or 2, wherein the liquid nasal carrier comprises a buffering agent.

5. The pharmaceutical composition of claim 4, wherein the buffering agent is selected from the group consisting of sodium citrate, sodium acetate, sodium phosphate, potassium phosphate and mixtures thereof.

6. The pharmaceutical composition of claim 5, wherein the composition has a pH of about 3 to 5.

7. The pharmaceutical composition of claim 1 or 2, wherein the buffering agent is present in the composition in a total amount of about 0.01% to 3% by weight.

8. The pharmaceutical composition of claim 1 or 2, wherein the liquid nasal carrier comprises an aqueous diluent.

9. The pharmaceutical composition of claim 8, wherein the aqueous diluent is selected from the group consisting of saline, water, dextrose or combinations thereof.

10. The pharmaceutical composition of claim 1 or 2, wherein the composition has a pH of about 3 to about 5.

11. The pharmaceutical composition of claim 1 or 2, wherein the composition has a pH of about 3 to about 5.

12. The pharmaceutical composition of claim 1 or 2, wherein the composition has a pH of about 4.

* * * * *